(12) United States Patent
Fryknas et al.

(10) Patent No.: US 11,504,356 B2
(45) Date of Patent: Nov. 22, 2022

(54) TREATMENT FOR INFLAMMATORY DISEASE

(71) Applicant: REPOS PHARMA AB, Uppsala (SE)

(72) Inventors: Marten Fryknas, Uppsala (SE); Rolf Larsson, Uppsala (SE); Peter Nygren, Uppsala (SE)

(73) Assignee: REPOS PHARMA AB, Uppsala (SE)

( * ) Notice: Subject to any disclaimer, the term of this patent is extended or adjusted under 35 U.S.C. 154(b) by 23 days.

(21) Appl. No.: 16/955,081

(22) PCT Filed: Dec. 19, 2018

(86) PCT No.: PCT/EP2018/085963
§ 371 (c)(1),
(2) Date: Jun. 18, 2020

(87) PCT Pub. No.: WO2019/121996
PCT Pub. Date: Jun. 27, 2019

(65) Prior Publication Data
US 2021/0015797 A1    Jan. 21, 2021

(30) Foreign Application Priority Data
Dec. 19, 2017  (GB) ..................................... 1721287

(51) Int. Cl.
A61K 31/4184 (2006.01)
A61P 37/00 (2006.01)
A61K 45/06 (2006.01)

(52) U.S. Cl.
CPC .......... *A61K 31/4184* (2013.01); *A61P 37/00* (2018.01); *A61K 45/06* (2013.01)

(58) Field of Classification Search
CPC ............................ A61K 31/4184; A61P 37/00
See application file for complete search history.

(56) References Cited

FOREIGN PATENT DOCUMENTS

| CN | 1748677 A | 3/2006 |
| CN | 1748678 A | 3/2006 |
| WO | 2008/036747 A2 | 3/2008 |
| WO | 2016127168 A2 | 8/2016 |
| WO | WO-2016196401 A1 * | 12/2016 ............. A61K 31/19 |

OTHER PUBLICATIONS

Office Action issued in corresponding Indian Patent Application 202047028751 dated Jan. 20, 2022 (with English translation) (9 pages).
Albonico et al., "Efficacy of mebendazole and levamisole alone or in combination against intestinal nematode infections after repeated targeted mebendazole treatment in Zanzibar," Bulletin of the World Health Organization, 2003, vol. 81, No. 5, pp. 343-352.
PCT Search Report and Written Opinion issued in corresponding International Application No. PCT/EP2018/085963 dated Jul. 10, 2019 (23 pages).
UKIPO Search Report issued in corresponding GB Application No. GB1721287.9 dated Aug. 30, 2018 (6 pages).
Mizuno et al, "Stimulation of pro-inflammatory responses by mebendazole in human monocytic THP-1 cells through an ERK signaling pathway," Archives of Toxicology, 2011, vol. 85:3, pp. 199-207.
Issa et al, "DrugGenEx-Net: a novel computational platform for systems pharmacology and gene expression-based drug repurposing," BMC Bioinformatics, 2016, vol. 17:202, pp. 1-18.
Judson, "Advances in the diagnosis and treatment of sarcoidosis," F1000Prime Reports, Oct. 2014, vol. 6, pp. 1-8.
Iyer et al, "Biological Evaluation of Mebendazone and Levamisole for Anti-Inflammatory and Anti-Ulcerative Properties," Indian Drugs, 1993 vol. 31:7, pp. 302-306.
Feria, "Immunomodulation in bronchial asthma," Algeria, 1980, vol. 27:1, pp. 37-44 (Abstract Only).
Wang et al, "Human autoimmune diseases: a comprehensive update," Journal of Internal Medicine, 2015, vol. 278, pp. 369-395.

* cited by examiner

*Primary Examiner* — Kevin E Weddington
(74) *Attorney, Agent, or Firm* — Kilyk & Bowersox, P.L.L.C.

(57) ABSTRACT

The invention provides mebendazole for use in the treatment or prophylaxis of a chronic inflammatory disease, and in particular wherein the chronic inflammatory disease is an autoimmune disease, for example sarcoidosis, systemic lupus erythematosus (SLE), Huntington's disease, end stage renal disease, systemic sclerosis (also called scleroderma), myositis, diabetes type 1, multiple sclerosis, Sjögren's syndrome, rheumatoid arthritis, psoriasis, primary biliary cirrhosis, autoimmune hepatitis, Graves' disease, Addison's disease, tuberculosis, Crohn's disease, ulcerative colitis, inflammatory bowel disease, Alzheimer's disease and coeliac disease. A method for the treatment or prophylaxis of a chronic inflammatory disease, comprising administering an effective amount of a mebendazole or a pharmaceutical composition of mebendazole is also provided. The use of mebendazole for the manufacture of a medicament for the treatment of a chronic inflammatory disease is also provided.

14 Claims, 6 Drawing Sheets

Mebendazole for 6 days at 100 mg x 2　　　Mebendazole 71 ng/ml at a dose of 200 mg x 2

TREATMENT FOR INFLAMMATORY DISEASE

This application is a National Stage Application of PCT/EP2018/085963, filed Dec. 19, 2018, which claims priority to United Kingdom Patent Application No. 1721287.9, filed Dec. 19, 2017.

FIELD OF INVENTION

The present invention relates to the treatment or prophylaxis of chronic inflammatory diseases (for example autoimmune diseases), in particular sarcoidosis and systemic lupus erythematosus (SLE). The treatments of the invention involve administering mebendazole to a patient suffering from a chronic inflammatory disease.

BACKGROUND OF INVENTION

Inflammation is part of the normal biological response to harmful stimuli, such as tissue damage, pathogens and irritants. Chronic inflammation may develop as a result of persistent stimuli such as irritants or pathogens or as a result of immune system dysfunction for example in autoimmune diseases.

Chronic Inflammatory diseases (CIDs) are a diverse array of conditions and disorders that are characterised by the presence of chronic inflammation. CIDs can cause significant and long term suffering. Many CIDs are autoimmune diseases. Examples of CIDs include dermatomyositis, Grave's disease, multiple sclerosis, myasthenia gravis, systemic lupus erythematosus (SLE), sarcoidosis, Sjögren's syndrome, amyloidosis, Hashimoto thyroiditis, vasculitis, rheumatoid arthritis, reactive arthritis, polymyositis, scleroderma, Addison's disease, vitiligo, pernicious anemia, glomerulonephritis, celiac gravis, diabetes type 1, psoriasis and pulmonary fibrosis (MedlinePlus medical encyclopedia—autoimmune disorders, National Institutes of Health; https://medlineplus.gov/ency/article/000816.htm; reviewed on 21 May 2017; accessed 24 November 2017).

Treatments of CIDs vary on a condition by condition basis. Sarcoidosis is a CID that causes small patches of red and swollen tissue (granulomas) to develop in the organs of the body. It usually affects the lungs and skin. The symptoms of sarcoidosis depend on which organs are affected, but typically include cough, feeling breathless, red or painful eyes, swollen glands, skin rashes, pain in joints, muscles or bones, and numbness or weakness of the face, arms, and legs. (Information from Sarcoidosis UK website http://sarcoidosisuk.org/ accessed 24 Nov. 2017). Treatments of sarcoidosis include Prednisone, hydroxychloroquine or chloroquine, and immunosuppressants, for example methotrexate, azathioprine, or leflunomide (information from National Heart, Lung and Blood Institute website https://www.nhlbi.nih.gov/health/health-topics/topics/sarc/treatment accessed 24 Nov. 2017).

Systemic lupus erythematosus (also referred to as "SLE" or simply "Lupus") is an autoimmune disease characterized by acute and chronic inflammation of various tissues of the body. Common lupus symptoms and signs include fatigue, low-grade fever, loss of appetite, muscle aches, hair loss, arthritis, ulcers of the mouth and nose, facial rash ("butterfly rash"), unusual sensitivity to sunlight (photosensitivity), chest pain caused by inflammation of the lining that surrounds the lungs (pleuritis) and the heart (pericarditis), and poor circulation to the fingers and toes with cold exposure (Raynaud's phenomenon). Treatments of SLE include non-steroidal anti-inflammatory drugs (NSAIDs), corticosteroids, immunosuppressants, hydroxychloroquine, and methotrexate. There is no known cure for SLE and none of the current treatments are completely effective in controlling the disease.

For most CIDs, the currently-available treatments are incompletely effective. There remains a significant need for further, more effective treatments. In particular, there remains a need for safe and well-tolerated treatments having manageable side-effects.

Mebendazole is an anti-parasitic agent that is clinically used for treatment of various forms of helminthic diseases. The structure of mebendazole is as follows:

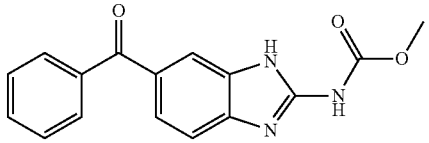 [SMILES: COC(=O)Nc1nc2ccc(C(=O)c3ccccc3)cc2[nH]1]

Mebendazole has been used extensively for local gut helminthic infections at low dose (Vermox®; 100 mg single dose, up to 100 mg×2 for up to 5 days depending on strain) but also at considerably higher doses, e.g. 40 mg/kg/day, over months to years against invasive echinococcus infections (Luder P. J., et al, Eur J Clin Pharmacol 31:443-448, 1986; Witassek, F., et al, Eur J Clin Pharmacol 20:427-433, 1981; Woodtli, W., et al, Am J Trop Med Hyg 34:754-760, 1985; WHO: Guidelines for treatment of cystic and alveolar echinococcosis in humans. Bull World Health Org 74:231-242, 1996).

The present inventors have discovered that mebendazole finds utility in the treatment of CIDs, for example autoimmune diseases, and in particular CIDs mediated by impaired ERK activity and/or decreased ERK signalling and/or inactivation of ERK, such as sarcoidosis and SLE.

SUMMARY OF THE INVENTION

The present invention provides mebendazole for use in the treatment of a chronic inflammatory disease (CID). For example, the CID is an autoimmune disease. For example, the CID is selected from sarcoidosis, Huntington's disease, psoriasis, multiple sclerosis, primary biliary cirrhosis, autoimmune hepatitis, Graves' disease, Crohn's disease, ulcerative colitis, coeliac disease, Addison's disease, Sjögren's syndrome, systemic lupus erythematosus (SLE) and rheumatoid arthritis. For example, the CID is sarcoidosis, psoriasis, multiple sclerosis, primary biliary cirrhosis, autoimmune hepatitis, Graves' disease, Crohn's disease, ulcerative colitis, coeliac disease, Addison's disease, Sjögren's syndrome, systemic lupus erythematosus (SLE) and rheumatoid arthritis. For example, the CID is sarcoidosis and systemic lupus erythematosus (SLE). For example, the CID is characterised by granulomatous inflammation. For example, the CID is sarcoidosis.

Also, for example, the CID is selected from systemic lupus erythematosus (SLE), Huntington's disease, end stage renal disease, sarcoidosis, systemic sclerosis (also called scleroderma), myositis, diabetes type 1, multiple sclerosis, Sjögren's syndrome, rheumatoid arthritis, psoriasis, primary biliary cirrhosis, autoimmune hepatitis, Graves' disease, Addison's disease, tuberculosis, Crohn's disease, ulcerative colitis, inflammatory bowel disease and Alzheimer's disease. For example, the CID is selected from systemic lupus erythematosus (SLE), Huntington's disease, end stage renal disease, sarcoidosis, systemic sclerosis (also called scleroderma), myositis, diabetes type 1, multiple sclerosis, Sjögren's syndrome, rheumatoid arthritis, psoriasis, primary biliary cirrhosis, autoimmune hepatitis, Graves' disease, Addison's disease, and tuberculosis. For example, the CID is selected from systemic lupus erythematosus (SLE), Huntington's disease, end stage renal disease, and sarcoidosis.

The present invention further provides mebendazole for use in the treatment of a CID, wherein the therapeutic dose of mebendazole administered to a patient is 1 mg to 4000 mg, 10 mg to 3000 mg, 10 mg to 2000 mg, 10 mg to 1000 mg, 10 mg to 750 mg, 10 mg to 500 mg, 20 to 400 mg, 25 mg to 300 mg, or 30 mg to 200 mg. Preferably, the therapeutic dose administered achieves a plasma concentration of mebendazole in a patient of 1 ng/ml to 1000 ng/ml (for example, 1 ng/ml to 900 ng/ml, 1 ng/ml to 800 ng/ml, 1 ng/ml to 750 ng/ml, 1 ng/ml to 600 ng/ml, 1 ng/ml to 500 ng/ml, 1 ng/ml to 400 ng/ml, 1 ng/ml to 300 ng/ml, 1 ng/ml to 200 ng/ml, or 1 ng/ml to 100 ng/ml; or, for example, 100 ng/ml to 900 ng/ml, 100 ng/ml to 800 ng/ml, 100 ng/ml to 750 ng/ml, 100 ng/ml to 600 ng/ml, 100 ng/ml to 500 ng/ml, 100 ng/ml to 400 ng/ml, 100 ng/ml to 300 ng/ml, or 100 ng/ml to 200 ng/ml; or, for example, 250 ng/ml to 900 ng/ml, 250 ng/ml to 800 ng/ml, 250 ng/ml to 750 ng/ml, 250 ng/ml to 600 ng/ml, or 250 ng/ml to 500 ng/ml; or, for example, 100 ng/ml to 900 ng/ml, 250 ng/ml to 900 ng/ml, 400 ng/ml to 900 ng/ml, 400 ng/ml to 800 ng/ml, or 400 ng/ml to 700 ng/ml or 400 ng/ml to 600 ng/ml)

In one embodiment, the therapeutic dose administered achieves a plasma concentration of mebendazole in a patient of 20 ng/ml to 100 ng/ml (for example 20 ng/ml to 40 ng/ml, 40 ng/ml to 60 ng/ml, 60 ng/ml to 80 ng/ml or 80 ng/ml to 100 ng/ml). In another embodiment, the therapeutic dose administered achieves a plasma concentration of mebendazole in a patient of 50 to 250 ng/ml (for example, 50 ng/ml to 100 ng/ml, 50 ng/ml to 150 ng/ml, 100 ng/ml to 200 ng/ml, 150 ng/ml to 200 ng/ml, or 200 ng/ml to 250 ng/ml). In another embodiment, the therapeutic dose administered achieves a plasma concentration of mebendazole in a patient of 100 ng/ml to 500 ng/ml (for example 100 ng/ml to 200 ng/ml, 200 ng/ml to 300 ng/ml, 300 ng/ml to 400 ng/ml, or 400 ng/ml to 500 ng/ml). In another embodiment, the therapeutic dose administered achieves a plasma concentration of mebendazole in a patient of 250 to 750 ng/ml (for example, 250 ng/ml to 400 ng/ml, 300 ng/ml to 450 ng/ml, 350 ng/ml to 500 ng/ml, 400 ng/ml to 550 ng/ml, or 450 ng/ml to 600 ng/ml). In another embodiment, the therapeutic dose administered achieves a plasma concentration of mebendazole in a patient of 500 to 1000 ng/ml (for example, 500 ng/ml to 600 ng/ml, 600 ng/ml to 700 ng/ml, 700 ng/ml to 800 ng/ml, 800 ng/ml to 900 ng/ml, or 900 ng/ml to 1000 ng/ml).

In a further embodiment, the therapeutic dose administered achieves a plasma concentration of mebendazole in a patient of 1 ng/ml to 400 ng/ml, 1 ng/ml to 300 ng/ml, 1 ng/ml to 200 ng/ml, 1 ng/ml to 100 ng/ml, preferably 20 ng/ml to 40 ng/ml, 40 ng/ml to 60 ng/ml, 60 ng/ml to 80 ng/ml or 80 ng/ml to 100 ng/ml.

The present invention further provides a pharmaceutical composition comprising mebendazole for use in the treatment of a CID, for example an autoimmune disease.

The present invention further provides a method for the treatment or prophylaxis of a CID, for example an autoimmune disease, comprising administering an effective amount or a pharmaceutical composition comprising mebendazole to a patient suffering from a CID. Preferably the patient is a human.

The present invention further provides a pharmaceutical composition comprising mebendazole in combination with at least one additional active component selected from the group consisting of non-steroidal anti-inflammatory drugs (NSAIDs), corticosteroids, immunosuppressants and disease-modifying anti-rheumatic drugs (DMARDs).

The present invention further provides the use of mebendazole for the manufacture of a medicament for the treatment of a CID, for example autoimmune diseases.

DETAILED DESCRIPTION OF INVENTION

Figure 1:
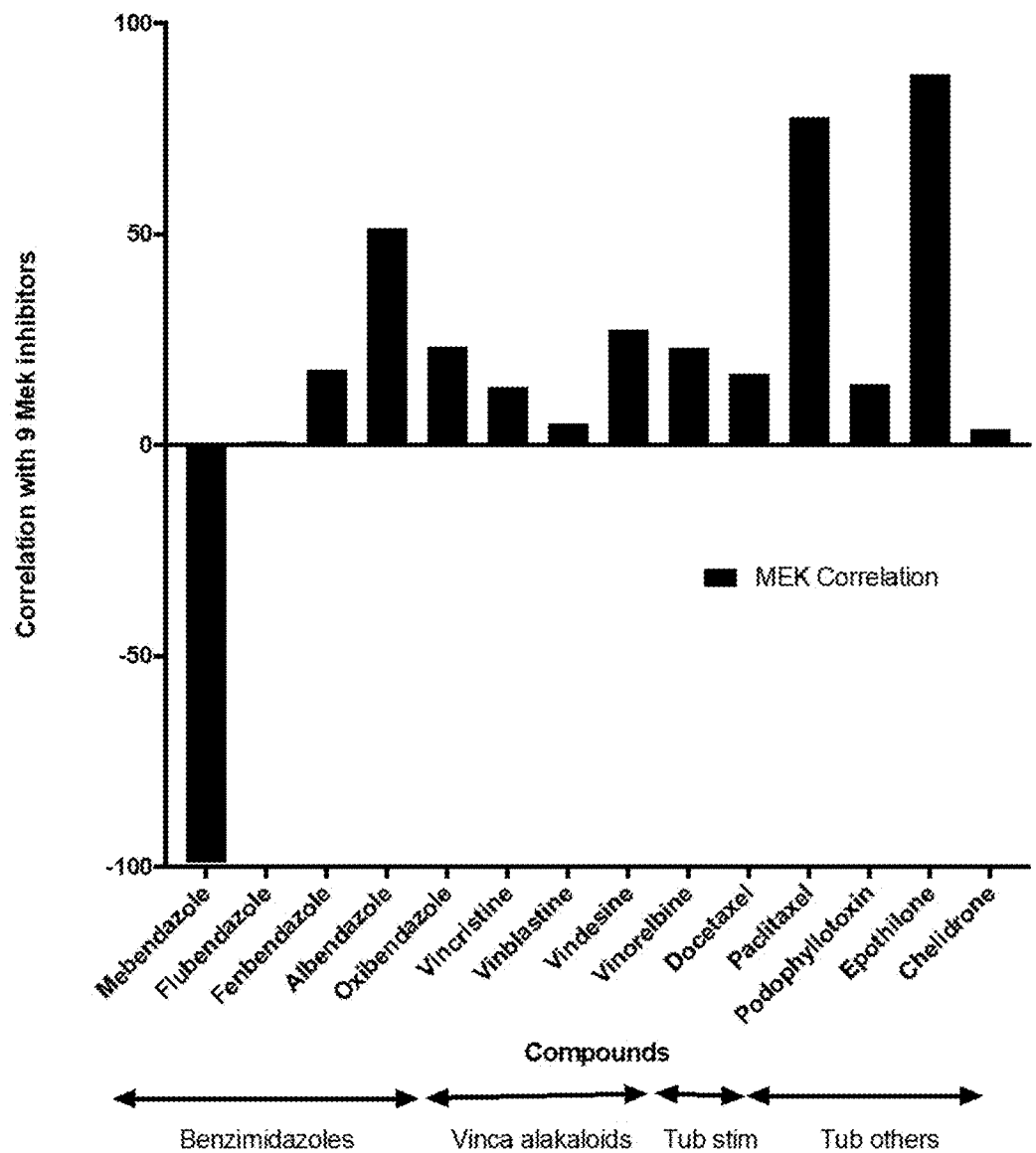
FIG. 1 shows the correlation of changes in gene expression (referred to as a "signature") induced by mebendazole and other tubulin-active agents with MEK/ERK inhibitors.

The inventors of the present invention have surprisingly found that mebendazole has particularly beneficial properties for use in the treatment or prophylaxis of chronic inflammatory diseases (CIDs). In particular, the inventors of the present invention have surprisingly found that mebendazole has particularly beneficial properties for use in the treatment or prophylaxis of a CID (in particular an autoimmune disease CID) wherein the CID is associated with impaired ERK activity and/or decreased ERK signalling and/or inactivation of ERK, and preferably wherein the CID is mediated by (for example, caused by or brought about by) impaired ERK activity and/or decreased ERK signalling and/or inactivation of ERK (e.g. it is a CID that may be treated or prevented by increasing ERK activity and/or increasing ERK signalling and/or activation of ERK). More particularly, the inventors of the present invention have surprisingly found that mebendazole has particularly beneficial properties for use in the treatment or prophylaxis of a CID that is associated with defective ERK signalling (for example, the CID is a disease brought about by defects in ERK signalling), and/or is associated with increased Type-1 interferon (interferon alpha and/or beta) response from plasmacytoid dendritic cells or other immune cells, and/or is associated with increased p38 MAP kinase signalling.

CIDs are a diverse array of conditions and disorders that are characterised by chronic inflammation. Many CIDs are autoimmune diseases. Inflammation is part of the normal biological response to harmful stimuli, such as tissue damage, pathogens or irritants. Inflammation can be classified as acute or chronic. Acute inflammation is the initial protective response to a harmful stimuli. Chronic inflammation may develop as a result of persistent stimuli such as irritants or pathogens, or as a result of immune system dysfunction for example in autoimmune diseases.

In many cases, chronic inflammation may result in the destruction of body tissue, abnormal growth of an organ and/or changes in organ function. Chronic inflammation comprises granulomatous, purulent, serous and/or ulcerative inflammation. Granulomatous inflammation is characterised by the formation of granulomas. Granulomas are tumour-like masses comprising immune cells such as macrophages and lymphocytes (e.g. natural killer cells, T-cells and B-cells). Purulent inflammation is characterised by accumulation of pus comprising dead cells, fluid and immune cells. Serous inflammation is characterised in the accumulation of serous fluid. Ulcerative inflammation is characterised by necrosis of epithelial tissue to form an ulcer.

The inflammatory response is closely regulated by intracellular signalling pathways, such as the mitogen-activated protein kinase (MAPK) pathway. The MAPK pathway comprises proteins referred to as mitogen-activated protein kinases (MAPKs). The MAPKs can be categorised into three major protein families, namely the extracellular signal-regulated kinase (ERK), c-Jun N-terminal kinase/stress-activated protein kinases (JNK/SAPKs) and p-38 proteins. Other proteins involved in the MAPK pathway include Ras, Raf and MEK.

Defects in ERK signalling have been implicated in chronic inflammatory diseases, for example in sarcoidosis, SLE, Huntington's disease and end stage renal disease (Gorelik G., Richardson B., Autoimmunity 2010; 43:17-22; Sawalha A. H., et al., Genes Immun 2008; 9:368-378; Maher P., et al., Hum Mol Genet 2010; 20:261-270; Huang L., et al., Immun Ageing 2017; 14:14; and Rastogi R., et al., Am J Respir Crit Care Med 2011; 183:500-510).

For example, inhibition of ERK signalling by agents such as hydralazine has been shown to induce lupus and lupus-like autoimmune diseases (Gorelik G., Richardson B., Autoimmunity 2010; 43:17-22; Sawalha A H, et al., Genes Immun 2008; 9:368-378). Further, decreased ERK expression in CD4+ T-cell obtained from a patient suffering from sarcoidosis has been reported (Celada L. J., et al., Am J Respir Crit Care Med 191; 2015:A3747). Abnormalities in the function of MAPKs such as ERK may be a result of loss-of-function mutations, gain-of-function mutations, decreased MAPK expression and/or increased MAPK expression. In the present invention, it is especially preferred that the mebendazole is for use in the treatment or prophylaxis of a CID, wherein the CID is a disease brought about by defects in ERK signalling.

As discussed in more detail below, the present inventors have surprisingly found that mebendazole very significantly increases the levels of p-ERK in monocytoid cells and macrophage cells. This is especially surprising because other tubulin-active agents, including other benzimidazoles such as fenbendazole, do not significantly increase p-ERK levels in those cells. The present inventors have also surprisingly found that mebendazole increases the activity of ERK in peripheral blood mononuclear cells (PBMC), and in CD4+ T-cells obtained from a patient suffering from SLE. The present inventors have also demonstrated that mebendazole is effective in the treatment of patients suffering from sarcoidosis, and effective in the treatment of SLE in a mouse model. Without wishing to be bound by any one theory, the present inventors believe mebendazole increases the activity of ERK, which in turn reduces inflammation in a patient suffering from a CID, such as SLE, sarcoidosis, Huntington's disease and end stage renal failure. As described in detail above, it is known that defects in ERK signalling have been implicated with those diseases. Thus, preferably the CID for treatment in the present invention is CID associated with defective ERK signalling, and more particularly a CID brought about by defects in ERK signalling.

Furthermore, many autoimmune diseases are driven (and potentially caused) by increased Type-1 interferon (interferon alpha and/or beta) response from plasmacytoid dendritic cells, or other immune cells. This response can be inhibited by ERK activation (Janovec V., et al., Front Immunol 2018; 9:364; Yang H-T., et al., J Immunol 2011; 186:1989-1996). Thus, mebendazole may be useful for treatment of an autoimmune disease, and in particular a CID, that is associated with increased Type-1 interferon (interferon alpha and/or beta) response from plasmacytoid dendritic cells, or other immune cells. Examples of such diseases include systemic sclerosis (also called scleroderma), myositis, diabetes type 1, multiple sclerosis, Sjögren's syndrome, psoriasis, primary biliary cirrhosis, autoimmune hepatitis, Graves' disease, Addison's disease, and tuberculosis (see, for example, Ronnblom L., Eloranta M-L., Curr Opin Rheumatol 2013; 25:248-253; Brkic Z., et al., Ann Rheum Dis 2016; 75:1567-1573; Crow M. K., Arthritis Res Ther 2010; 12 Suppl 1:S5; Namiki K., et al., J Biol Chem 2012; 287:24228-24238; Toro-Dominguez D., et al., Arthritis Res Ther 2014; 16:325-8; Schett G., et al., Ann Rheum Dis 2008; 67:909-916; Nestle F. O., et al., J Exp Med 2005; 202:135-143; Yao Y., et al., PLoS ONE 2008; 3:e2737; Takii Y., et al., Lab Invest 2005; 85:908-920; Israel J., et al., Saudi J Gastroenterol 2011; 17:348-9; Ruiz-Riol M., et al., Journal of Autoimmunity 2011; 36:189-200; Krysiak R., et al., The American Journal of the Medical Sciences 2011; 341:504-507; and Maertzdorf J., et al., Proc Natl Acad Sci USA 2012; 109:7853-7858)

Increased P38 MAP kinase signalling is also known to be a key driver for inflammation in several autoimmune diseases (Kumar S., et al., Nat Rev Drug Discov 2003; 2:717-726). ERK activation can downregulate p38 MAP kinase signalling by induction of dual specificity phosphatase (MKP-1) (Kondoh K., et al., Biochim Biophys Acta 2007; 1773:1227-1237; and Toulouse A., et al., Neural Regen Res 2015; 10:1748-1749). Thus, mebendazole may be useful for treatment of an autoimmune disease, and in particular a CID, that is associated with increased p38 MAP kinase signalling. Examples of such diseases include Crohn's disease, ulcerative colitis, inflammatory bowel disease (IBD) and Alzheimer's disease. (Feng Y. J., Li Y. Y., J Dig Dis 2011; 12:327-332; and Waetzig G. H., et al., The Journal of Immunology 2002; 168:5342-5351; Munoz L, Ammit A J., Neuropharmacology 2010; 58:561-568).

Mebendazole

Mebendazole has been used as an anthelmintic since 1971. It is known to be safe and well-tolerated at low dose. The safety of low-dose mebendazole (Vermox) was evaluated in 6276 subjects who participated in 39 clinical trials for the treatment of single or mixed parasitic infestations of the gastrointestinal tract. In these 39 clinical trials, related adverse events occurred in less than 1% of mebendazole-treated subjects. Long-term high-dose (40 mg/kg/day) treatment with mebendazole for invasive parasitic invasion is also known to be generally well tolerated with transient hair loss, gastrointestinal problems, elevated but reversible transaminases and mild leukopenia and thrombocytopenia as outstanding adverse events (Woodtli, W., et al, Am J Trop Med Hyg 34:754-760, 1985; WHO: Guidelines for treatment of cystic and alveolar echinococcosis in humans. Bull World Health Org 74:231-242, 1996; Davis, A., et al, Bull World Health Org 67:503-508, 1989).

The established good tolerance and safety profile of mebendazole is an additional advantage of using mebendazole in the treatment of CIDs.

Although mebendazole is well-established for treating various forms of helminthic diseases, there have been no reports of it being effective against any CIDs associated with impaired ERK activity and/or decreased ERK signalling and/or inactivation of ERK.

Mebendazole has the following structure:

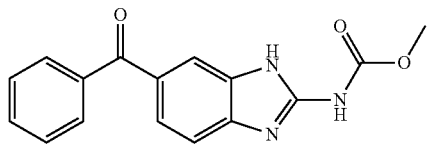 [SMILES: COC(=O)Nc1nc2ccc(C(=O)c3ccccc3)cc2[nH]1]

The CAS ID for mebendazole is 31431-39-7. Mebendazole is sold as a pharmaceutical composition for oral administration under the trade name Vermox. In Vermox the mebendazole is the free base form. Mebendazole for use in the methods and treatments of present invention may also be in the form of a salt, solvate or prodrug. Mebendazole has various polymorphs. Mebendazole for use in the methods and treatments of present invention may be in any polymorph form. Preferably mebendazole is in polymorph form A and/or B and/or C, and more preferably mebendazole is in polymorph form C or polymorph form A and/or C.

Salts of mebendazole which are suitable for use in the present invention are those wherein a counterion is pharmaceutically acceptable. Suitable salts include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxalic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids, while not in themselves pharmaceutically acceptable, may be useful as intermediates in obtaining the compounds of the invention and their pharmaceutical acceptable acid addition salts.

Particular salts of mebendazole include acid addition salts such as those formed from hydrochloric, hydrobromic, acetic, p-toluenesulfonic, tartaric, sulphuric, succinic, phosphoric, oxalic, nitric, methanesulfonic, malic, maleic and citric acid, and in particular hydrochloric acid.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Mebendazole used in the present invention may be in the form of a solvate.

A compound which, upon administration to the recipient, is capable of being converted into mebendazole, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference. As described above, the mebendazole for use in the embodiments of the present invention may be in the form of a prodrug.

Mebendazole for use in the embodiments of the present invention is preferably in the form of a pharmaceutical composition. Pharmaceutical compositions useful according to the invention include those suitable for oral, parenteral (including subcutaneous, intradermal, intramuscular, intravenous (bolus or infusion), and intraarticular), inhalation (including fine particle dusts or mists which may be generated by means of various types of metered dose pressurized aerosols), nebulizers or insufflators, rectal, intraperitoneal and topical (including dermal, buccal, sublingual, and intraocular) administration, although the most suitable route may depend upon, for example, the condition and disorder of the recipient. Preferably, the pharmaceutical composition is suitable for oral administration.

Pharmaceutical compositions of the present invention suitable for oral administration may be presented as discrete units such as capsules, cachets or tablets each containing a predetermined amount of mebendazole; as a powder or granules; as a solution or a suspension in an aqueous liquid or a non-aqueous liquid; or as an oil-in-water liquid emulsion or a water-in-oil liquid emulsion. Mebendazole may also be presented as a bolus, electuary or paste. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42:2S, 1988.

For oral administration, mebendazole is preferably provided as a pharmaceutical composition in the form of tablets or other forms of presentation provided in discrete units containing 1.0, 2.5, 5.0, 10.0, 15.0, 25.0, 50.0, 100, 250, 500 or 1000 mg of the mebendazole for the symptomatic adjustment of the dosage to the patient to be treated. A medicament comprising mebendazole typically contains from about 10 mg to about 1000 mg of mebendazole, preferably from about 10 mg to about 500 mg of mebendazole, for example 50, 100, 200, 400 or 500 mg of mebendazole. Intravenously, the most preferred doses will range from about 0.1 to about 50 mg/kg/minute during a constant rate infusion. Mebendazole may be administered in a single daily therapeutic dose, or may be administered in two, three or four or more times daily as split doses to provide the daily therapeutic dose. Preferably, mebendazole is administered in two daily split doses to provide the daily therapeutic dose.

Compositions for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Pharmaceutical compositions for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Compositions for topical administration in the mouth, for example buccally or sublingually, include lozenges comprising mebendazole in a flavoured basis such as sucrose and acacia or tragacanth, and pastilles comprising mebendazole in a basis such as gelatin and glycerine or sucrose and acacia. Exemplary compositions for topical administration include a topical carrier such as Plastibase (mineral oil gelled with polyethylene).

Preferred unit dosage compositions are those containing an exploratory dose or therapeutic dose, as hereinbefore recited, or an appropriate fraction thereof, of mebendazole.

It should be understood that in addition to the ingredients particularly mentioned above, the compositions of this invention may include other agents conventional in the art having regard to the type of composition in question, for example those suitable for oral administration may include flavouring agents.

Whilst mebendazole, or salt thereof, for use in the various embodiments of the present invention may be used as the sole active ingredient, it is also possible for mebendazole to be used in combination with one or more further active agents. Thus, the invention also provides mebendazole for use in the treatment of CIDs, or for use in methods of treatment of CIDs, according to the invention together with a further active agent, for simultaneous, sequential or separate administration. Such further active agents may be agents useful in the treatment of a CID, or other pharmaceutically active materials, but are preferably agents known for the treatment of CIDs such as autoimmune diseases. Such agents are known in the art. Particular examples of further therapeutic agents for use in the present invention include non-steroidal anti-inflammatory drugs (NSAIDs), corticosteroids, immunosuppressants and disease-modifying antirheumatic drugs (DMARDs), for example hydroxychloroquine, methotrexate, prednisone, azathioprine and leflunomide.

When used in a combination, the precise dosage of the further active agent(s) will vary with the dosing schedule, the oral potency of the particular agent chosen, the age, size, sex and condition of the subject/patient (typically a mammal or human; preferably a human), the nature and severity of the condition, and other relevant medical and physical factors. Thus, a precise pharmaceutically effective amount can be readily determined by the caregiver or clinician. An appropriate amount can be determined by routine experimentation from animal models and human clinical studies. For humans, an effective dose will be known or otherwise able to be determined by one of ordinary skill in the art.

The individual components of such combinations can be administered separately at different times during the course of therapy or concurrently in divided or single combination forms. The present invention is therefore to be understood as embracing all such regimes of simultaneous or alternating treatment.

The above further active agent(s), when employed in combination with compounds useful in the invention, may be used, for example, in those amounts indicated in the Physicians' Desk Reference (PDR) or as otherwise determined by one of ordinary skill in the art.

Chronic Inflammatory Diseases

The present invention provides mebendazole, or a salt thereof, for use in treatment of a CID. In one embodiment of the invention, the CID is selected from acne, acid reflux/heartburn, age related macular degeneration (AMD), allergy, Alzheimer's disease, amyotrophic lateral sclerosis, anaemia, appendicitis, arteritis, asthma, atherosclerosis, balanitis, blepharitis, bronchiolitisa bullous pemphigoid, burn, bursitis, carditis, celiac disease, cellulitis, cervicitis, cholangitis, cholecystitis, chorioamnionitis, chronic obstructive pulmonary disease (COPD), cirrhosis (such as primary biliary cirrhosis), colitis (such as ulcerative colitis), congestive heart failure, conjunctivitis, cyclophosphamide-induced cystitis, cystic fibrosis, cystitis, common cold, Crohn's disease, dacryoadenitis, dementia, dermatitis, dermatomyositis, digestive system disease, eczema, emphysema, encephalitis, endocarditis, endometritis, enteritis, enterocolitis, epicondylitis, epididymitis, fasciitis, fibromyalgia, fibrosis, fibrositis, foreign body granuloma, gastritis, gastroenteritis, gingivitis, glomerulonephritis, glossitis, heart disease, heart valve dysfunction, hepatitis (such as autoimmune hepatitis), hidradenitis suppurativa, Huntington's disease, hyperlipidemic pancreatitis, hypertension, ileitis, infection (e.g. viral, bacterial, fungal), inflammatory bowel disease, inflammatory cardiomegaly, inflammatory neuropathy, inflammatory lung diseases, neuropathy insulin resistance, interstitial cystitis, interstitial nephritis, iritis, ischemia, ischemic heart disease, keratitis, keratoconjunctivitis, laryngitis, systemic lupus erythematosus, lupus nephritis, mastitis, mastoiditis, meningitis, metabolic syndrome (syndrome X), a migraine, multiple sclerosis, myelitis, myocarditis, myositis, neurological disorders, nephritis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, phlebitis, pleuritis, pneumonitis, polycystic nephritis, proctitis, prostatitis, psoriasis, pulpitis, pyelonephritis, pylephlebitis, renal failure, reperfusion injury, retinitis, rheumatic fever, salpingitis, sarcoidosis, sialadenitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumour, urethritis, ursitis, uveitis, vaginitis, vasculitis, and vulvitis. The CID may also be selected from diabetes type 1, systemic sclerosis (also called scleroderma), Sjögren's syndrome, rheumatoid arthritis, Grave's disease, Addison's disease and end stage renal disease. In certain preferred embodiments, the CID is a CID characterised by granulomatous inflammation.

In one embodiment of the invention, the CID is selected from Alzheimer's disease, cirrhosis (such as primary biliary cirrhosis), colitis (such as ulcerative colitis), Crohn's disease, hepatitis (such as autoimmune hepatitis), Huntington's disease, inflammatory bowel disease, systemic lupus erythematosus, multiple sclerosis, myositis, psoriasis, renal failure (for example end stage renal disease), sarcoidosis and tuberculosis. The CID may also be selected from diabetes type 1, systemic sclerosis (also called scleroderma), Sjögren's syndrome, rheumatoid arthritis, Grave's disease and Addison's disease.

In one embodiment of the invention, the CID is selected from Alzheimer's disease, cirrhosis (such as primary biliary cirrhosis), colitis (such as ulcerative colitis), Crohn's disease, hepatitis (such as autoimmune hepatitis), Huntington's disease, inflammatory bowel disease, systemic lupus erythematosus, multiple sclerosis, myositis, psoriasis, renal failure (for example end stage renal disease), sarcoidosis and tuberculosis. The CID may also be selected from diabetes type 1, systemic sclerosis (also called scleroderma), Sjögren's syndrome, Grave's disease and Addison's disease.

In one embodiment of the invention, the CID is selected from Alzheimer's disease, cirrhosis (such as primary biliary cirrhosis), colitis (such as ulcerative colitis), Crohn's disease, hepatitis (such as autoimmune hepatitis), Huntington's disease, inflammatory bowel disease, systemic lupus erythematosus, myositis, renal failure (for example end stage renal disease), sarcoidosis and tuberculosis. The CID may also be selected from diabetes type 1, systemic sclerosis (also called scleroderma), and Addison's disease.

In one embodiment of the invention, the CID is selected from Alzheimer's disease, cirrhosis (such as primary biliary cirrhosis), colitis (such as ulcerative colitis), Crohn's disease, hepatitis (such as autoimmune hepatitis), Huntington's disease, inflammatory bowel disease, myositis, renal failure (for example end stage renal disease), sarcoidosis and tuberculosis. The CID may also be selected from diabetes type 1, systemic sclerosis (also called scleroderma), and Addison's disease.

In one embodiment of the invention, the CID is a disease associated with impaired ERK activity and/or decreased ERK signalling and/or inactivation of ERK (and more preferably the CID is a disease mediated by impaired ERK activity and/or decreased ERK signalling and/or inactivation of ERK (e.g. the CID is a disease that may be treated or prevented by increasing ERK activity and/or increasing ERK signalling and/or activation of ERK)); and/or the CID is associated with defective ERK signalling (for example, the CID is brought about by defects in ERK signalling), and/or is associated with increased Type-1 interferon (interferon alpha and/or beta) response from plasmacytoid dendritic cells or other immune cells, and/or is associated with increased p38 MAP kinase signalling. Examples of such CIDs include systemic lupus erythematosus (SLE), Huntington's disease, end stage renal disease, sarcoidosis, systemic sclerosis (also called scleroderma), myositis, diabetes type 1, multiple sclerosis, Sjögren's syndrome, rheumatoid arthritis, psoriasis, primary biliary cirrhosis, autoimmune hepatitis, Graves' disease, Addison's disease, tuberculosis, Crohn's disease, ulcerative colitis, inflammatory bowel disease and Alzheimer's disease.

In one embodiment of the invention, the CID is a disease caused by impaired ERK activity and/or decreased ERK signalling and/or inactivation of ERK (e.g. the CID is a disease that may be treated or prevented by increasing ERK activity and/or increasing ERK signalling and/or activation of ERK); and/or the CID is associated with defective ERK signalling (for example, the CID is brought about by defects in ERK signalling), and/or is associated with increased Type-1 interferon (interferon alpha and/or beta) response from plasmacytoid dendritic cells or other immune cells, and/or is associated with increased p38 MAP kinase signalling. Examples of such CIDs include systemic lupus erythematosus (SLE), Huntington's disease, end stage renal disease, sarcoidosis, systemic sclerosis (also called scleroderma), myositis, diabetes type 1, multiple sclerosis, Sjögren's syndrome, rheumatoid arthritis, psoriasis, primary biliary cirrhosis, autoimmune hepatitis, Graves' disease, Addison's disease, tuberculosis, Crohn's disease, ulcerative colitis, inflammatory bowel disease and Alzheimer's disease.

In certain preferred embodiments, the CID is a disease associated with impaired ERK activity and/or decreased ERK signalling and/or inactivation of ERK (and more preferably the CID is a disease mediated by impaired ERK activity and/or decreased ERK signalling and/or inactivation of ERK (e.g. the CID is a disease that may be treated or prevented by increasing ERK activity and/or increasing ERK signalling and/or activation of ERK)); and/or the CID is associated with defective ERK signalling (for example, the CID is brought about by defects in ERK signalling), and/or is associated with increased Type-1 interferon (interferon alpha and/or beta) response from plasmacytoid dendritic cells or other immune cells, and/or is associated with increased p38 MAP kinase signalling, and the CID is selected from the group consisting of:

systemic lupus erythematosus (SLE), Huntington's disease, end stage renal disease, sarcoidosis, systemic sclerosis (also called scleroderma), myositis, diabetes type 1, multiple sclerosis, Sjögren's syndrome, rheumatoid arthritis, psoriasis, primary biliary cirrhosis, autoimmune hepatitis, Graves' disease, Addison's disease, tuberculosis, Crohn's disease, ulcerative colitis, inflammatory bowel disease and Alzheimer's disease; or systemic lupus erythematosus (SLE), Huntington's disease, end stage renal disease, sarcoidosis, systemic sclerosis (also called scleroderma), myositis, diabetes type 1, multiple sclerosis, Sjögren's syndrome, psoriasis, primary biliary cirrhosis, autoimmune hepatitis, Graves' disease, Addison's disease, tuberculosis, Crohn's disease, ulcerative colitis, inflammatory bowel disease and Alzheimer's disease; or systemic lupus erythematosus (SLE), Huntington's disease, end stage renal disease, sarcoidosis, systemic sclerosis (also called scleroderma), myositis, diabetes type 1, primary biliary cirrhosis, autoimmune hepatitis, Addison's disease, tuberculosis, Crohn's disease, ulcerative colitis, inflammatory bowel disease and Alzheimer's disease; or Huntington's disease, end stage renal disease, sarcoidosis, systemic sclerosis (also called scleroderma), myositis, diabetes type 1, primary biliary cirrhosis, autoimmune hepatitis, Addison's disease, tuberculosis, Crohn's disease, ulcerative colitis, inflammatory bowel disease and Alzheimer's disease.

In certain preferred embodiments, the CID is a disease associated with impaired ERK activity and/or decreased ERK signalling and/or inactivation of ERK (and more preferably the CID is a disease mediated by impaired ERK activity and/or decreased ERK signalling and/or inactivation of ERK (e.g. the CID is a disease that may be treated or prevented by increasing ERK activity and/or increasing ERK signalling and/or activation of ERK)); and/or the CID is associated with defective ERK signalling (for example, the CID is brought about by defects in ERK signalling), and/or is associated with increased Type-1 interferon (interferon alpha and beta) response from plasmacytoid dendritic cells or other immune cells and the CID is selected from the group consisting of:

systemic lupus erythematosus (SLE), Huntington's disease, end stage renal disease, sarcoidosis, systemic sclerosis (also called scleroderma), myositis, diabetes type 1, multiple sclerosis, Sjögren's syndrome, rheumatoid arthritis, psoriasis, primary biliary cirrhosis, autoimmune hepatitis, Graves' disease, Addison's disease, and tuberculosis; or systemic lupus erythematosus (SLE), Huntington's disease, end stage renal disease, sarcoidosis, systemic sclerosis (also called scleroderma), myositis, diabetes type 1, multiple sclerosis, Sjögren's syndrome, psoriasis, primary biliary cirrhosis, autoimmune hepatitis, Graves' disease, Addison's disease, and tuberculosis; or systemic lupus erythematosus (SLE), Huntington's disease, end stage renal disease, sarcoidosis, systemic sclerosis (also called scleroderma), myositis, diabetes type 1, primary biliary cirrhosis, autoimmune hepatitis, Addison's disease, and tuberculosis; or Huntington's disease, end stage renal disease, sarcoidosis, systemic sclerosis (also called scleroderma), myositis, diabetes type 1, primary biliary cirrhosis, autoimmune hepatitis, Addison's disease, and tuberculosis.

In certain preferred embodiments, the CID is a disease associated with impaired ERK activity and/or decreased ERK signalling and/or inactivation of ERK (and more preferably the CID is a disease mediated by impaired ERK activity and/or decreased ERK signalling and/or inactivation of ERK (e.g. the CID is a disease that may be treated or prevented by increasing ERK activity and/or increasing ERK signalling and/or activation of ERK)); and/or the CID is associated with defective ERK signalling (for example, the CID is brought about by defects in ERK signalling), and the CID is selected from the group consisting of:

systemic lupus erythematosus (SLE), Huntington's disease, end stage renal disease, and sarcoidosis; or Huntington's disease, end stage renal disease, and sarcoidosis; or Autoimmune Diseases In an embodiment of the invention, the CID is an autoimmune disease. For example the CID is an autoimmune disease selected from dermatomyositis, Grave's disease, multiple sclerosis, myasthenia gravis, systemic lupus erythematosus (SLE), sarcoidosis, Sjögren syndrome, amyloidosis, Hashimoto thyroiditis, vasculitis, rheumatoid arthritis, reactive arthritis, polymyositis, scleroderma (also known as systemic sclerosis), Addison's disease, vitiligo, pernicious anaemia, glomerulonephritis, celiac gravis, pulmonary fibrosis, Huntington's disease, Crohn's disease and primary biliary cirrhosis. For example, the CID is an autoimmune disease selected from Grave's disease, multiple sclerosis, systemic lupus erythematosus (SLE), sarcoidosis, Sjögren's syndrome, rheumatoid arthritis, scleroderma (also known as systemic sclerosis), Addison's disease, Huntington's disease, Crohn's disease and primary biliary cirrhosis. Preferably, the autoimmune disease is selected from systemic lupus erythematosus and sarcoidosis.

In one embodiment of the invention, the CID is an autoimmune disease, and for example is selected from sarcoidosis, Huntington's disease, psoriasis, multiple sclerosis, primary biliary cirrhosis, autoimmune hepatitis, Graves' disease, Crohn's disease, ulcerative colitis, coeliac disease, Addison's disease, Sjögren's syndrome, systemic lupus erythematosus (SLE) and rheumatoid arthritis. For example, the CID is an autoimmune disease and is sarcoidosis, psoriasis, multiple sclerosis, primary biliary cirrhosis, autoimmune hepatitis, Graves' disease, Crohn's disease, ulcerative colitis, coeliac disease, Addison's disease, Sjögren's syndrome, systemic lupus erythematosus (SLE) and rheumatoid arthritis. For example, the CID is an autoimmune disease and is sarcoidosis and systemic lupus erythematosus (SLE). For example, the CID is an autoimmune disease characterised by granulomatous inflammation. For example, the CID is the autoimmune diseases sarcoidosis.

In another embodiment, the CID is an autoimmune disease, and for example is selected from sarcoidosis, Huntington's disease, psoriasis, multiple sclerosis, primary biliary cirrhosis, autoimmune hepatitis, Graves' disease, Crohn's disease, ulcerative colitis, Addison's disease, Sjögren's syndrome, and systemic lupus erythematosus (SLE). For example, the CID is an autoimmune disease and is sarcoidosis, psoriasis, multiple sclerosis, primary biliary cirrhosis, autoimmune hepatitis, Graves' disease, Crohn's disease, ulcerative colitis, Addison's disease, Sjögren's syndrome, and systemic lupus erythematosus (SLE). For example, the CID is an autoimmune disease and is sarcoidosis and systemic lupus erythematosus (SLE). For example, the CID is an autoimmune disease characterised by granulomatous inflammation. For example, the CID is the autoimmune disease sarcoidosis.

In another embodiment, the CID is an autoimmune disease, and for example is selected from sarcoidosis, Huntington's disease, primary biliary cirrhosis, autoimmune hepatitis, Crohn's disease, ulcerative colitis, Addison's disease, and systemic lupus erythematosus (SLE). For example, the CID is an autoimmune disease and is sarcoidosis, primary biliary cirrhosis, autoimmune hepatitis, Crohn's disease, ulcerative colitis, Addison's disease, and systemic lupus erythematosus (SLE). For example, the CID is sarcoidosis and systemic lupus erythematosus (SLE). For example, the CID is an autoimmune disease characterised by granulomatous inflammation. For example, the CID is the autoimmune disease sarcoidosis.

In another embodiment, the CID is an autoimmune disease, and for example is selected from sarcoidosis, Huntington's disease, primary biliary cirrhosis, autoimmune hepatitis, Crohn's disease, ulcerative colitis, and Addison's disease. For example, the CID is an autoimmune disease and is sarcoidosis, primary biliary cirrhosis, autoimmune hepatitis, Crohn's disease, ulcerative colitis, and Addison's disease. For example, the CID is an autoimmune disease characterised by granulomatous inflammation. For example, the CID is the autoimmune disease sarcoidosis.

In one especially preferred embodiment, the CID is an autoimmune disease and is selected from systemic lupus erythematosus (SLE), Huntington's disease, end stage renal disease, sarcoidosis, systemic sclerosis (also called scleroderma), myositis, diabetes type 1, multiple sclerosis, Sjögren's syndrome, rheumatoid arthritis, psoriasis, primary biliary cirrhosis, autoimmune hepatitis, Graves' disease, Addison's disease, tuberculosis, Crohn's disease, ulcerative colitis, inflammatory bowel disease and Alzheimer's disease. More preferably, the CID is an autoimmune disease and is selected from systemic lupus erythematosus (SLE), Huntington's disease, end stage renal disease, sarcoidosis, systemic sclerosis (also called scleroderma), myositis, diabetes type 1, multiple sclerosis, Sjögren's syndrome, rheumatoid arthritis, psoriasis, primary biliary cirrhosis, autoimmune hepatitis, Graves' disease, Addison's disease, and tuberculosis. Even more preferably, the CID is an autoimmune disease and is selected from systemic lupus erythematosus (SLE), Huntington's disease, end stage renal disease, and sarcoidosis. For example, the CID is an autoimmune disease and is selected from systemic lupus erythematosus (SLE) and sarcoidosis.

In another especially preferred embodiment, the CID is an autoimmune disease and is selected from systemic lupus erythematosus (SLE), Huntington's disease, end stage renal disease, sarcoidosis, systemic sclerosis (also called scleroderma), myositis, diabetes type 1, multiple sclerosis, Sjögren's syndrome, psoriasis, primary biliary cirrhosis, autoimmune hepatitis, Graves' disease, Addison's disease, tuberculosis, Crohn's disease, ulcerative colitis, inflammatory bowel disease and Alzheimer's disease. More preferably, the CID is an autoimmune disease and is selected from systemic lupus erythematosus (SLE), Huntington's disease, end stage renal disease, sarcoidosis, systemic sclerosis (also called scleroderma), myositis, diabetes type 1, multiple sclerosis, Sjögren's syndrome psoriasis, primary biliary cirrhosis, autoimmune hepatitis, Graves' disease, Addison's disease, and tuberculosis. Even more preferably, the CID is an autoimmune disease and is selected from systemic lupus erythematosus (SLE), Huntington's disease, end stage renal disease, and sarcoidosis. For example, the CID is an autoimmune disease and is selected from systemic lupus erythematosus (SLE) and sarcoidosis.

In a further especially preferred embodiment, the CID is an autoimmune disease and is selected from systemic lupus erythematosus (SLE), Huntington's disease, end stage renal disease, sarcoidosis, systemic sclerosis (also called scleroderma), myositis, diabetes type 1, primary biliary cirrhosis, autoimmune hepatitis, Addison's disease, tuberculosis, Crohn's disease, ulcerative colitis, inflammatory bowel disease and Alzheimer's disease. More preferably, the CID is an autoimmune disease and is selected from systemic lupus erythematosus (SLE), Huntington's disease, end stage renal disease, sarcoidosis, systemic sclerosis (also called scleroderma), myositis, diabetes type 1, primary biliary cirrhosis, autoimmune hepatitis, Addison's disease, and tuberculosis. Even more preferably, the CID is an autoimmune disease and is selected from systemic lupus erythematosus (SLE), Huntington's disease, end stage renal disease, and sarcoidosis. For example, the CID is an autoimmune disease and is selected from systemic lupus erythematosus (SLE) and sarcoidosis.

In a further especially preferred embodiment, the CID is an autoimmune disease and is selected from Huntington's disease, end stage renal disease, sarcoidosis, systemic sclerosis (also called scleroderma), myositis, diabetes type 1, primary biliary cirrhosis, autoimmune hepatitis, Addison's disease, tuberculosis, Crohn's disease, ulcerative colitis, inflammatory bowel disease and Alzheimer's disease. More preferably, the CID is an autoimmune disease and is selected from, Huntington's disease, end stage renal disease, sarcoidosis, systemic sclerosis (also called scleroderma), myositis, diabetes type 1, primary biliary cirrhosis, autoimmune hepatitis, Graves' disease, Addison's disease, and tuberculosis. Even more preferably, the CID is an autoimmune disease and is selected from Huntington's disease, end stage renal disease, and sarcoidosis. For example, the CID is the autoimmune disease sarcoidosis.

Types of Inflammation

In an embodiment of the invention, the CID is characterised by the presence of granulomatous, purulent, serous and/or ulcerative inflammation. Preferably, the CID is characterised by the presence of granulomatous inflammation. CIDs that may be characterised by the presence of granulomatous inflammation include sarcoidosis, tuberculosis, Crohn's disease, hepatic granulomatous disease, histiocytosis disorders, orofacial granulomatosis, Blau's syndrome and foreign body granulomas such as beryllium granuloma, zirconium granuloma, silica granuloma and talc granuloma. For example, the CID is sarcoidosis or tuberculosis, and especially is sarcoidosis.

In certain preferred embodiments, the CID is a disease associated with impaired ERK activity and/or decreased ERK signalling and/or inactivation of ERK (and more preferably the CID is a disease mediated by impaired ERK activity and/or decreased ERK signalling and/or inactivation of ERK (e.g. the CID is a disease that may be treated or prevented by increasing ERK activity and/or increasing ERK signalling and/or activation of ERK)); and/or the CID is associated with increased Type-1 interferon (interferon alpha and/or beta) response from plasmacytoid dendritic cells or other immune cells, and/or is associated with increased p38 MAP kinase signalling, and the CID is characterised by the presence of granulomatous, purulent, serous and/or ulcerative inflammation. Preferably, it is characterised by the presence of granulomatous inflammation. For example, the CID is sarcoidosis, tuberculosis, or Crohn's disease, and especially is sarcoidosis.

Mebendazole Therapeutic Dose

In certain embodiments of the invention, the use of mebendazole comprises administering a therapeutic dose of mebendazole to the patient. Preferably the patient is a human. A therapeutic dose of mebendazole may be administered repeatedly, for example daily, every second or third day, weekly, every second, third or fourth week or even as a high single therapeutic dose depending on the patient and the type of CID to be treated. A therapeutic dose of mebendazole may be administered repeatedly over a short period or a long period. For example the therapeutic dose may be repeatedly administrated over a period of days, weeks, months or years.

The amount of mebendazole which is required to achieve a therapeutic effect will vary with particular route of administration and the characteristics of the patient under treatment, for example the species, age, weight, sex, medical conditions, the particular disease and its severity, and other relevant medical and physical factors. An ordinarily skilled physician can readily determine and administer the effective amount of mebendazole required for treatment or prophylaxis of a CID.

Preferably the therapeutic dose of mebendazole is 1 mg to 4000 mg, preferably 10 mg to 3000 mg, more preferably 10 mg to 2000 mg. Preferably, the therapeutic dose of mebendazole may be 10 mg to 1000 mg, 10 mg to 750 mg, 10 mg to 500 mg, 20 to 400 mg, 25 mg to 300 mg, or 30 mg to 200 mg. Alternatively, the therapeutic dose of mebendazole may be 50 mg to 150 mg, 250 mg to 350 mg, 350 mg to 450 mg, 450 mg to 550 mg, 500 mg to 1000 mg, 1000 mg to 1500 mg, 1500 mg to 2000 mg, 2000 to 3000 mg, or 3000 to 4000 mg. For example the therapeutic dose of mebendazole may be, for example, 10, 20, 25, 30, 24, 50, 60, 70, 75, 80, 90, 95, 100, 105, 110, 120, 125, 130, 140, 150, 160, 170, 175, 180, 190, 200, 210, 220, 225, 250, 275, 300, 325, 350, 375, 400, 425, 450, 475, 500, 600, 700, 750, 800, 900, 1000, 1100, 1200, 1250, 1300, 1400, 1500, 1750, 2000, 2250, 2500, 2750, 3000, 3250, 3500, 3750, or 4000 mg. Preferably 50, 100, 200, 300, 400 or 500 mg. Most preferably 200 mg or 400 mg.

In certain embodiments, the therapeutic dose of mebendazole is administered as a single dose in a day. For example, for a therapeutic dose of 100 mg, a single 100 mg dose is administered. In certain embodiments, the therapeutic dose of mebendazole is administered as two or more split doses in a day. For example, for a therapeutic dose of 200 mg, a two 100 mg doses or four 50 mg doses may be administered in a day. As a further example, for a therapeutic dose of 400 mg, a two 200 mg doses or four 100 mg doses may be administered in a day. The therapeutic dose may be administered as two or more split doses in a day, for example 2, 3, 4, 5 or 6 split doses in a day, three or more split doses in a day, four or more split doses in a day, five or more split doses in a day or 6 or more split doses in a day. The therapeutic dose may be administered as up to 8 split doses in a day, or as up to 7 split doses in a day, as up to 6 split doses in a day, as up to 4 split doses in a day, as up to 3 split doses in a day, or as two split doses in a day. In preferred embodiments, the therapeutic dose of mebendazole may be administered as two split doses in a day.

In embodiments wherein the therapeutic dose of mebendazole is administered as two or more split doses in a day, the dose administered in each split therapeutic dose may be the same, for example, for a therapeutic dose of 100 mg, a two 50 mg doses. Alternatively, each split therapeutic dose may be difference, for example, for a therapeutic dose of 150 mg, one 50 mg dose and one 100 mg dose. Preferably the dose administered in each split therapeutic dose is the same.

Certain embodiments of the present invention comprise administering a therapeutic dose of mebendazole to the patient, wherein the dose is sufficient to achieve a certain plasma concentration of mebendazole.

The dose may be sufficient to achieve a plasma concentration of mebendazole of 1 ng/ml to 1000 ng/ml (for example, 1 ng/ml to 900 ng/ml, 1 ng/ml to 800 ng/ml, 1 ng/ml to 750 ng/ml, 1 ng/ml to 600 ng/ml, 1 ng/ml to 500 ng/ml, 1 ng/ml to 400 ng/ml, 1 ng/ml to 300 ng/ml, 1 ng/ml to 200 ng/ml, or 1 ng/ml to 100 ng/ml; or, for example, 100 ng/ml to 900 ng/ml, 100 ng/ml to 800 ng/ml, 100 ng/ml to 750 ng/ml, 100 ng/ml to 600 ng/ml, 100 ng/ml to 500 ng/ml, 100 ng/ml to 400 ng/ml, 100 ng/ml to 300 ng/ml, or 100 ng/ml to 200 ng/ml; or, for example, 250 ng/ml to 900 ng/ml, 250 ng/ml to 800 ng/ml, 250 ng/ml to 750 ng/ml, 250 ng/ml to 600 ng/ml, or 250 ng/ml to 500 ng/ml; or, for example, 100 ng/ml to 900 ng/ml, 250 ng/ml to 900 ng/ml, 400 ng/ml to 900 ng/ml, 400 ng/ml to 800 ng/ml, or 400 ng/ml to 700 ng/ml or 400 ng/ml to 600 ng/ml).

In one embodiment, the dose may be sufficient to achieve a plasma concentration of mebendazole of 20 ng/ml to 100 ng/ml (for example 20 ng/ml to 40 ng/ml, 40 ng/ml to 60 ng/ml, 60 ng/ml to 80 ng/ml or 80 ng/ml to 100 ng/ml). In another embodiment, the dose may be sufficient to achieve a plasma concentration of mebendazole of 50 to 250 ng/ml (for example, 50 ng/ml to 100 ng/ml, 50 ng/ml to 150 ng/ml, 100 ng/ml to 200 ng/ml, 150 ng/ml to 200 ng/ml, or 200 ng/ml to 250 ng/ml). In another embodiment, the dose may be sufficient to achieve a plasma concentration of mebendazole of 100 ng/ml to 500 ng/ml (for example 100 ng/ml to 200 ng/ml, 200 ng/ml to 300 ng/ml, 300 ng/ml to 400 ng/ml, or 400 ng/ml to 500 ng/ml). In another embodiment, the dose may be sufficient to achieve a plasma concentration of mebendazole of 250 to 750 ng/ml (for example, 250 ng/ml to 400 ng/ml, 300 ng/ml to 450 ng/ml, 350 ng/ml to 500 ng/ml, 400 ng/ml to 550 ng/ml, or 450 ng/ml to 600 ng/ml). In another embodiment, the dose may be sufficient to achieve a plasma concentration of mebendazole of 500 to 1000 ng/ml (for example, 500 ng/ml to 600 ng/ml, 600 ng/ml to 700 ng/ml, 700 ng/ml to 800 ng/ml, 800 ng/ml to 900 ng/ml, or 900 ng/ml to 1000 ng/ml).

In one embodiment, the dose may be sufficient to achieve a plasma concentration of mebendazole of is 1 ng/ml to 400 ng/ml, preferably 1 ng/ml to 300 ng/ml, preferably 1 ng/ml to 200 ng/ml, more preferably 1 ng/ml to 100 ng/ml. For example the plasma concentration of mebendazole is 1 ng/ml to 20 ng/ml, preferably 20 ng/ml to 40 ng/ml, preferably 40 ng/ml to 60 ng/ml, preferably 60 ng/ml to 80 ng/ml, preferably 80 ng/ml to 100 ng/ml. Most preferably 60 ng/ml to 80 ng/ml.

Certain embodiments of the present invention comprise administering a therapeutic dose of mebendazole to the patient, wherein the dose is sufficient to achieve a certain steady state maximum plasma concentration of mebendazole.

The dose may be sufficient to achieve a steady state maximum plasma concentration of mebendazole of 1 ng/ml to 1000 ng/ml (for example, 1 ng/ml to 900 ng/ml, 1 ng/ml to 800 ng/ml, 1 ng/ml to 750 ng/ml, 1 ng/ml to 600 ng/ml, 1 ng/ml to 500 ng/ml, 1 ng/ml to 400 ng/ml, 1 ng/ml to 300 ng/ml, 1 ng/ml to 200 ng/ml, or 1 ng/ml to 100 ng/ml; or, for example, 100 ng/ml to 900 ng/ml, 100 ng/ml to 800 ng/ml, 100 ng/ml to 750 ng/ml, 100 ng/ml to 600 ng/ml, 100 ng/ml to 500 ng/ml, 100 ng/ml to 400 ng/ml, 100 ng/ml to 300 ng/ml, or 100 ng/ml to 200 ng/ml; or, for example, 250 ng/ml to 900 ng/ml, 250 ng/ml to 800 ng/ml, 250 ng/ml to 750 ng/ml, 250 ng/ml to 600 ng/ml, or 250 ng/ml to 500 ng/ml; or, for example, 100 ng/ml to 900 ng/ml, 250 ng/ml to 900 ng/ml, 400 ng/ml to 900 ng/ml, 400 ng/ml to 800 ng/ml, or 400 ng/ml to 700 ng/ml or 400 ng/ml to 600 ng/ml).

In one embodiment, the dose may be sufficient to achieve a steady state maximum plasma concentration of mebendazole of 20 ng/ml to 100 ng/ml (for example 20 ng/ml to 40 ng/ml, 40 ng/ml to 60 ng/ml, 60 ng/ml to 80 ng/ml or 80 ng/ml to 100 ng/ml). In another embodiment, the dose may be sufficient to achieve a steady state maximum plasma concentration of mebendazole of 50 to 250 ng/ml (for example, 50 ng/ml to 100 ng/ml, 50 ng/ml to 150 ng/ml, 100 ng/ml to 200 ng/ml, 150 ng/ml to 200 ng/ml, or 200 ng/ml to 250 ng/ml). In another embodiment, the dose may be sufficient to achieve a steady state maximum plasma concentration of mebendazole of 100 ng/ml to 500 ng/ml (for example 100 ng/ml to 200 ng/ml, 200 ng/ml to 300 ng/ml, 300 ng/ml to 400 ng/ml, or 400 ng/ml to 500 ng/ml). In another embodiment, the dose may be sufficient to achieve a steady state maximum plasma concentration of mebendazole of 250 to 750 ng/ml (for example, 250 ng/ml to 400 ng/ml, 300 ng/ml to 450 ng/ml, 350 ng/ml to 500 ng/ml, 400 ng/ml to 550 ng/ml, or 450 ng/ml to 600 ng/ml). In another embodiment, the dose may be sufficient to achieve a steady state maximum plasma concentration of mebendazole of 500 to 1000 ng/ml (for example, 500 ng/ml to 600 ng/ml, 600 ng/ml to 700 ng/ml, 700 ng/ml to 800 ng/ml, 800 ng/ml to 900 ng/ml, or 900 ng/ml to 1000 ng/ml).

In one embodiment, the dose may be sufficient to achieve a steady state maximum plasma concentration of mebendazole of is 1 ng/ml to 400 ng/ml, preferably 1 ng/ml to 300 ng/ml, preferably 1 ng/ml to 200 ng/ml, more preferably 1 ng/ml to 100 ng/ml. For example the plasma concentration of mebendazole is 1 ng/ml to 20 ng/ml, preferably 20 ng/ml to 40 ng/ml, preferably 40 ng/ml to 60 ng/ml, preferably 60 ng/ml to 80 ng/ml, preferably 80 ng/ml to 100 ng/ml. Most preferably 60 ng/ml to 80 ng/ml.

The effectiveness of mebendazole for the treatment or prophylaxis of a chronic inflammatory disease is demonstrated in examples 2 to 7 below, which describe the activity of mebendazole to increase ERK signalling, effectively treat a patient suffering from sarcoidosis, and effectively treat a mouse model of SLE. Defective ERK signalling is implicated in many CIDs. Furthermore, ERK activation can inhibit other drivers of autoimmune diseases, such as increased Type-1 interferon (interferon alpha and/or beta) response from plasmacytoid dendritic cells (or other immune cells) and increased P38 MAP kinase signalling. As such, the data show that it can be expected that the present invention will be effective for the treatment of various CIDs, and in particular those associated with the above-mentioned pathways, and more generally those associated with (and preferably mediated by) impaired ERK activity and/or decreased ERK signalling and/or inactivation of ERK (e.g. CIDs that may be treated or prevented by increasing ERK activity and/or increasing ERK signalling and/or activation of ERK). Such CIDs include, in particular, sarcoidosis, SLE, Huntington's disease, end stage renal disease and rheumatoid arthritis; for example sarcoidosis, SLE, Huntington's disease, and end stage renal disease.

EXAMPLES

Examples 1 to 5

Materials

Mebendazole, albendazole, fenbendazole, oxibendazole, thiabendazole, vinblastine and PMA were purchased from Sigma, St. Louis, Mo. Vincristine and docetaxel were purchased from Selleckchem (Houston, Tex.). The compounds were kept as 10 mM stock solutions in dimethyl sulfoxide (DMSO, Sigma, St. Louis, Mo.) or sterile water and further diluted with culture medium as needed.

Cell Culture Method

Peripheral blood mononuclear cells (PBMCs) from healthy donors were isolated by 1.077 g/ml Ficoll-Paque centrifugation and cryopreserved as described by Larsson et al. (Int J Cancer 1992; 50: 177-185). Cell viability was determined by trypan blue exclusion test. SLE PBMCs were obtained Astarte Biologics, WA, USA (cat no 1035, lot 3429DE16) in cryopreserved vials (10 million cells). CD4+ cells were subsequently isolated with an autoMACS® instrument and a CD4+ isolation kit from Miltenyi Biotec according to the manufacturer's description and the method described by Gorelik et al. (J. Immunol. 2007; 179(8):5553-5563).

Monocytoid THP-1 cells were obtained from ATCC (Manassas, Va.) and were cultured in RPMI-1640 medium, supplemented with 10% heat-inactivated fetal bovine serum (HIFBS), 2 mM L-glutamine, 100 U/100 mg/mL penicillin/streptomycin and 0.05 mM 2-mercaptoethanol (all from Sigma, St Louis, Mo.). All cell lines were cultured at 37° C. in a humidified atmosphere containing 5% $CO_2$.

Measurement of Phospho-ERK 1/2 (p-ERK)

Phospho-ERK 1/2 (p-ERK) activity was measured using the Bioplex Pro Cell Signalling assay kit for ERK 1/2 (Biorad) and the Luminex MAGPIX® system according to the manufacturers' instructions. Measurements of p-ERK in CD4+ cells followed the protocol described by Gorelik et al. (J. Immunol. 2007; 179(8):5553-5563).

Example 1. Gene Expression Signatures of Mebendazole Compared to Those of MEK/ERK Inhibitors Using the LINCS Connectivity Map (CMap) Database The drug-induced gene expression perturbations of mebendazole were studied using the public LINCS Connectivity Map (CMap) database (www.clue.io) that contains a collection of hundreds-of-thousands of L1000 gene-expression profiles from cells grown in monolayer exposed to a large numbers of small-molecule and genetic perturbagens (www.clue.io). Since mebendazole is present in the database, the gene expression can be compared with other drugs and pertubargens.

Using the LINCS CMap database, the mebendazole signature was entered as a query to identify compounds that induce similar or opposite gene expression signature. For each compound query the database provides enrichment (correlation) scores based on Kormogorov Smirnov statistics (Lamb J et al. Science 2006; 313:1929-35) for sets of compounds representing different pharmacological classes. In the case of mebendazole a negative enrichment score of −99.05 was observed for the set of 9 MEK inhibitors: PD-198306 (ID 7950), MEK 1/2 inhibitor (ID 4279), U-0126 (ID 7490), U0126 (ID 9449), Selumetinib (ID 0016), PD-98059 (ID 0658), PD-0325901 (ID 5102), AS-703026 (ID 4967) and PD-184352 (ID 4563). This enrichment was mebendazole-specific and not shared by other benzimidazoles or tubulin inhibitors. These results indicate that mebendazole strongly induces MEK/ERK activation.

Example 2. The Effect of Mebendazole and Other Tubulin-Active Agents on p-ERK in Monocytoid THP-1 Cells Phosphorylation of ERK by upstream MAPK proteins such as MEK results in activation of ERK. Measurement of p-ERK levels in cells is used as an indicator of ERK signalling. The level of p-ERK in monocytoid THP-1 cells was measured using the Bioplex Pro Cell Signalling assay kit for ERK 1/2 (Biorad) and the Luminex MAGPIX® system. The assay is based on binding of the target of interest via antibodies to magnetic beads. The target is detected using biotinylated antibodies with a fluorescent reporter. The assay was performed according to the manufacturer's instructions.

Figure 2:
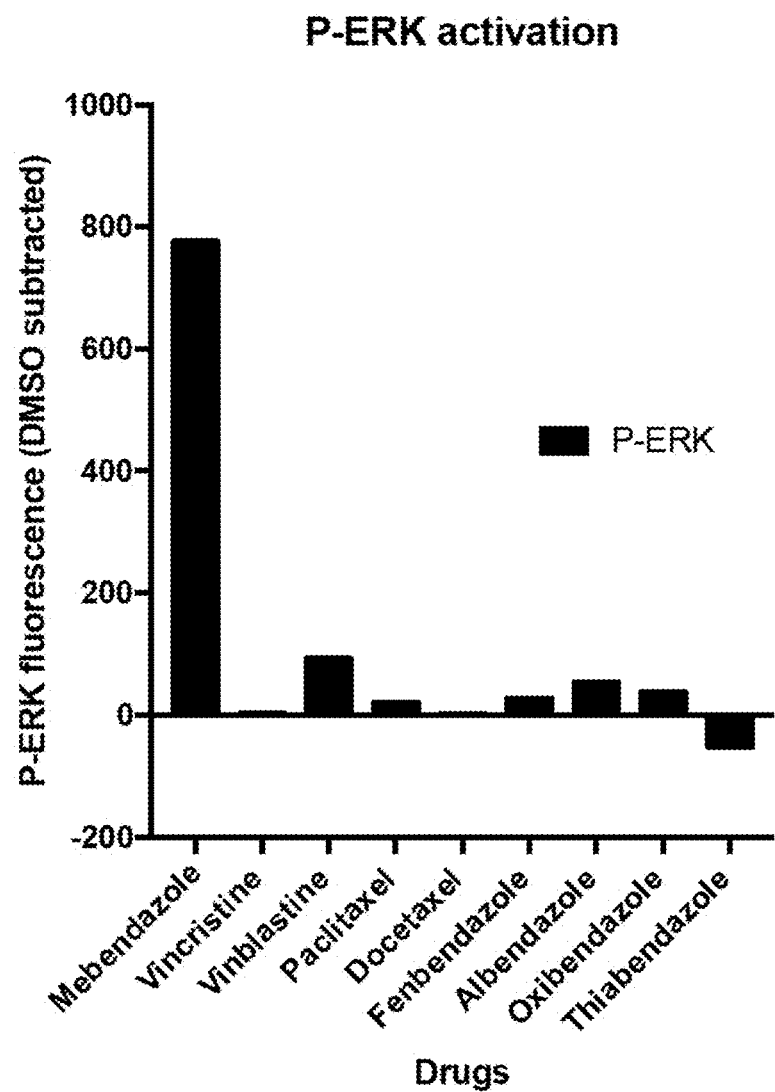
FIG. 2 shows the effect of mebendazole and other tubulin-active agents on phospho-ERK (p-ERK) in monocytoid THP-1 cells.

FIG. 2 shows the effect of mebendazole and other tubulin-active agents on p-ERK levels in THP-1 cells. Mebendazole significantly increased the levels of p-ERK in THP-1 cells. The other tubulin-active agents that were tested did not increase p-ERK levels in THP-1 cells.

Example 3. The Effect of Mebendazole on p-ERK in Monocytoid THP-1 Cells and Peripheral Blood Mononuclear Cells (PBMC) in the Presence of MEK/ERK Inhibitor U0126

The levels of p-ERK in monocytoid THP-1 cells and PBMC cells were measured using the Bioplex Pro Cell Signalling assay kit for ERK 1/2 (Biorad) and the Luminex MAGPIX® system. The assay is based on binding of the target of interest via antibodies to magnetic beads. The target is detected using biotinylated antibodies with a fluorescent reporter. The assay was performed according to the manufacturer instructions.

Figure 3:
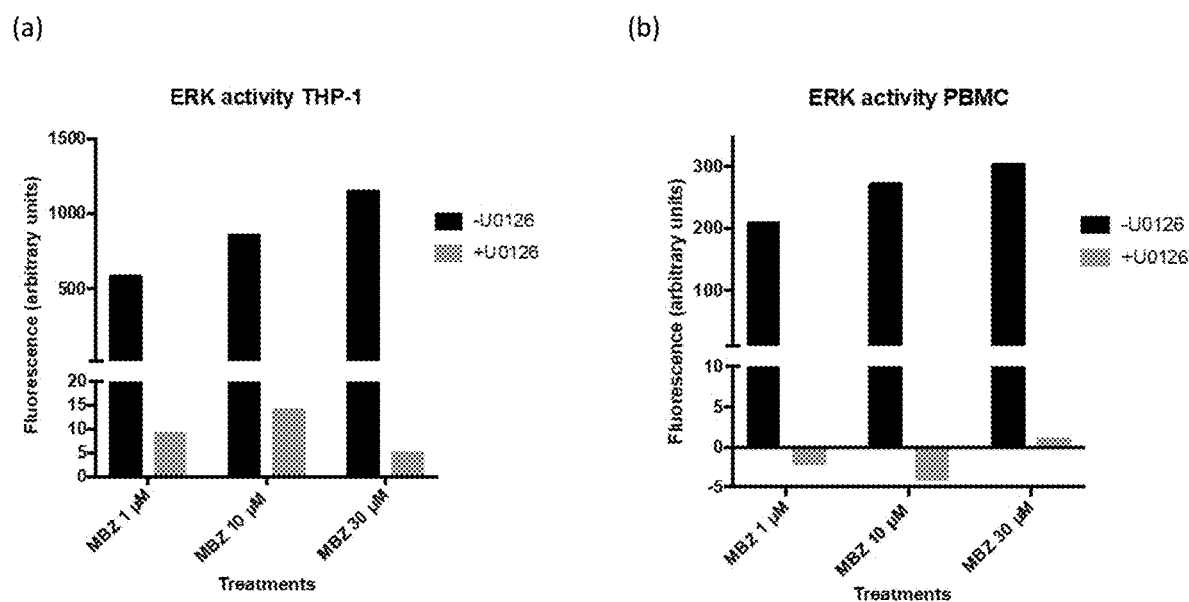
FIG. 3 shows the effect of mebendazole with and without the MEK/ERK inhibitor U0126 on p-ERK in monocytoid THP-1 cells (FIG. 3a) and peripheral blood mononuclear cells (PBMC) (FIG. 3b).

FIG. 3 shows the effect of mebendazole on p-ERK levels in THP-1 cells treated with and without MEK/ERK inhibitor U0126 (FIG. 3a) and PBMC cells treated with and without MEK/ERK inhibitor U0126 (FIG. 3b). In THP-1 cells not treated with U0126, the level of p-ERK increased with an increasing dose of mebendazole. At 1 μm mebendazole the fluorescence reading was approximately 500 arb units, and at 30 μM mebendazole the fluorescence reading increased to approximately 1200 arb units. In THP-1 cells treated with U0126, only a low level of p-ERK was detected with an approximate fluorescence reading of 5 to 15 arb units being recorded. These data show that mebendazole increases p-ERK level and therefore ERK activity in THP-1 cells and that this activation is ablated in the presence of U0126. A similar result was observed in PMBCs, where p-ERK levels increased with an increasing dose of mebendazole.

Example 4. The Effect of Mebendazole on p-ERK in CD4+ T-Cells Isolated from PBMCs from an SLE Patient Compared with CD4+ Cells Isolated from Normal PBMCs CD4+ T-Cells were isolated from PBMCs obtained from the venous blood of healthy donors and patients with SLE using the method described in Gorelik et al. (J. Immunol. 2007; 179(8):5553-5563). The level of p-ERK in the isolated CD4+ T-Cells was measured using the Bioplex Pro Cell Signalling assay kit for ERK 1/2 (Biorad) and the Luminex MAGPIX® system.

Figure 4:
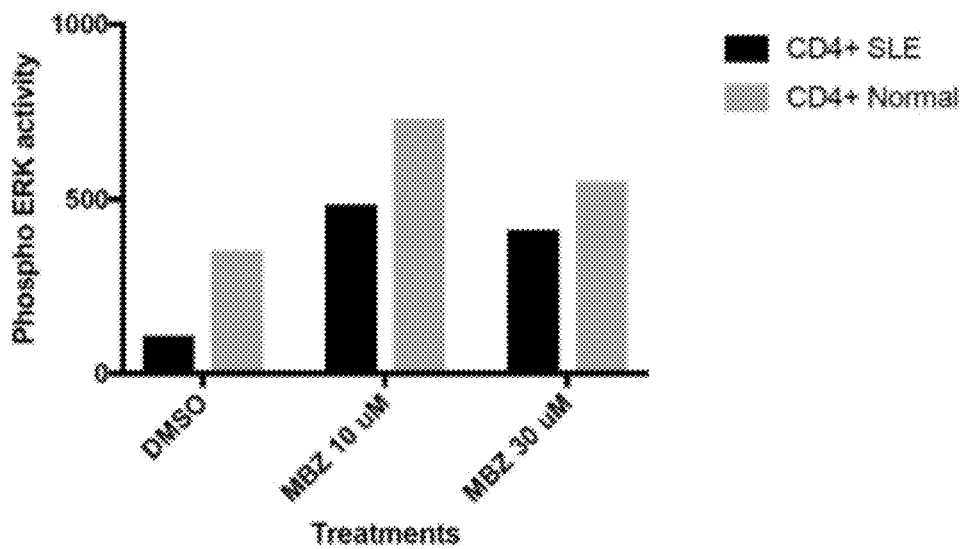
FIG. 4 shows the effect of mebendazole on p-ERK levels in CD4+ T-cells isolated from PBMCs from an SLE patient compared with CD4+ cells isolated from normal PBMCs.

As shown in FIG. 4, 10 μM and 30 μM of mebendazole administered to CD4+ T-cells restored the activity of p-ERK to at least the same level as that observed in CD4+ T-cells obtained from a healthy donor. This data suggest that mebendazole is capable of restoring the p-ERK activity in CD4+ T-cells obtained from patients with a CID resulting from defective p-ERK activity.

Example 5. Effect of Mebendazole and Fenbendazole in Monocytoid THP-1 Cells and PMA Differentiated THP-1 Macrophages on Phospho-ERK (p-ERK) Activity Phosphorylation of ERK by upstream MAPK proteins such as MEK results in activation of ERK. Measurement of p-ERK levels in cells is used as an indicator of ERK signalling. As such, in this example the effect of mebendazole and fenbendazole on p-ERK levels in monocytoid THP-1 cells and PMA differentiated THP-1 macrophages after exposure to either compound was studied.

The levels of the phosphoprotein phospho-ERK (p-ERK) in cell lysates after 1 h exposure to mebendazole (10 μM)), fenbendazole (10 μM) or control (DMSO) in monocytoid THP-1 cells and PMA differentiated THP-1 macrophages was measured using the Luminex MAGPIX® system and the commercially available kit (Biorad, Hercules, Calif.) described above. The assay is based on binding of the target of interest via antibodies to magnetic beads. The target is detected using biotinylated antibodies with a fluorescent reporter. The assays were performed according to the manufacturer's instructions. Briefly, the protein concentrations in the cell lysates were first determined using a Micro-BCA method (ThermoFischer Scientific, Waltham, Mass., USA) to ensure equal amounts of samples in the assay and then measurements were performed by incubating the cell lysate samples with beads, then with detection antibody, and finally with streptavidin-PE. The fluorescence was measured using the MAGPIX instrument (BioRad) and the concentration levels were determined by fitting to a standard curve.

Figure 5A:
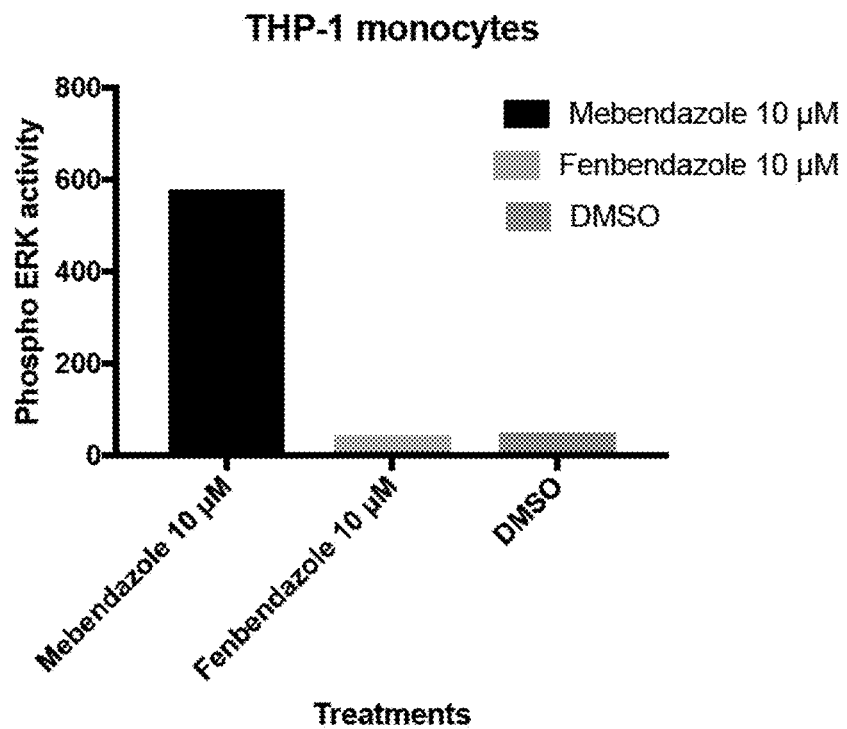
FIGS. 5a and 5b show the effect of mebendazole, fenbendazole and control (DMSO) on phospho-ERK (p-ERK) levels in THP-1 monocytes (FIG. 5a) and PMA differentiated THP-1 macrophages (FIG. 5b) after 1 hr exposure to mebendazole, fenbendazole or control (DMSO).
Figure 5B:
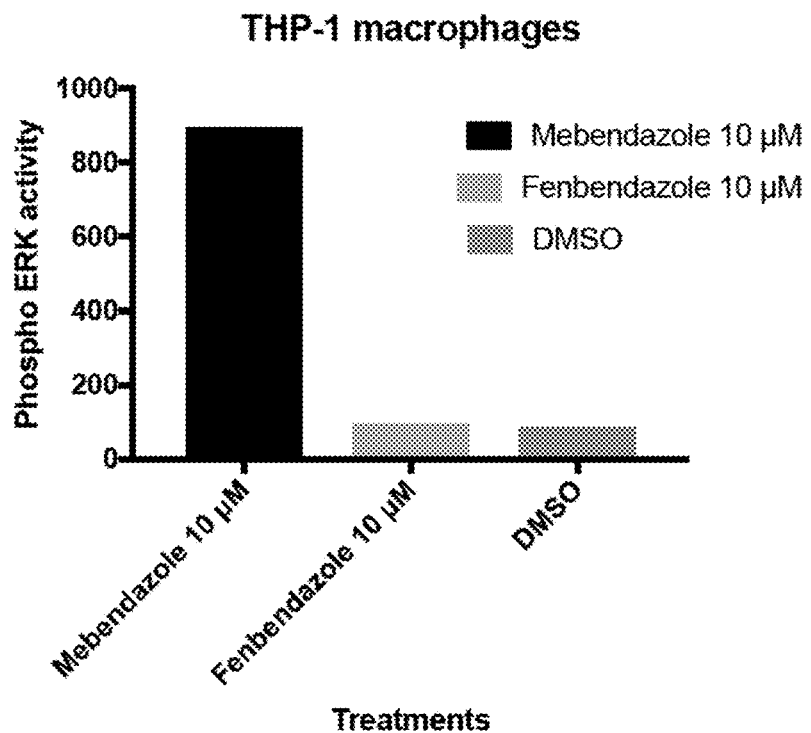

FIGS. 5a and 5b show the effect of mebendazole (10 μM), fenbendazole (10 μM) and control (DMSO) on p-ERK levels in monocytoid THP-1 cells (FIG. 5a) and PMA differentiated THP-1 macrophages (FIG. 5b) after 1 hr of exposure to mebendazole, fenbendazole or control (DMSO). Mebendazole significantly increased the levels of p-ERK in both THP-1 cell types. Fenbendazole did not increase p-ERK levels in either type of THP-1 cells.

Example 6. Treatment of Sarcoidosis Patient with Mebendazole

The patient was a male who was operated on for colon cancer at the age of 56 years. The patient suffered from a relapse with a liver metastasis one year later. He refused standard of care with chemotherapy and was started on experimental treatment with mebendazole instead. A daily dose of 200 mg (given as 2×100 mg) of mebendazole was administered for six consecutive days. At that point, a PET/CT examination was performed showing, in addition to the known liver metastasis, lung hilar enlargement and mediastinal lymph nodes with elevated FDG-signal compatible with the radiological diagnosis of sarcoidosis (involved tissue indicated with arrows; left panel in FIG. 6). This diagnosis was also suggested from previous CT scans at the time of the cancer operation.

Figure 6:
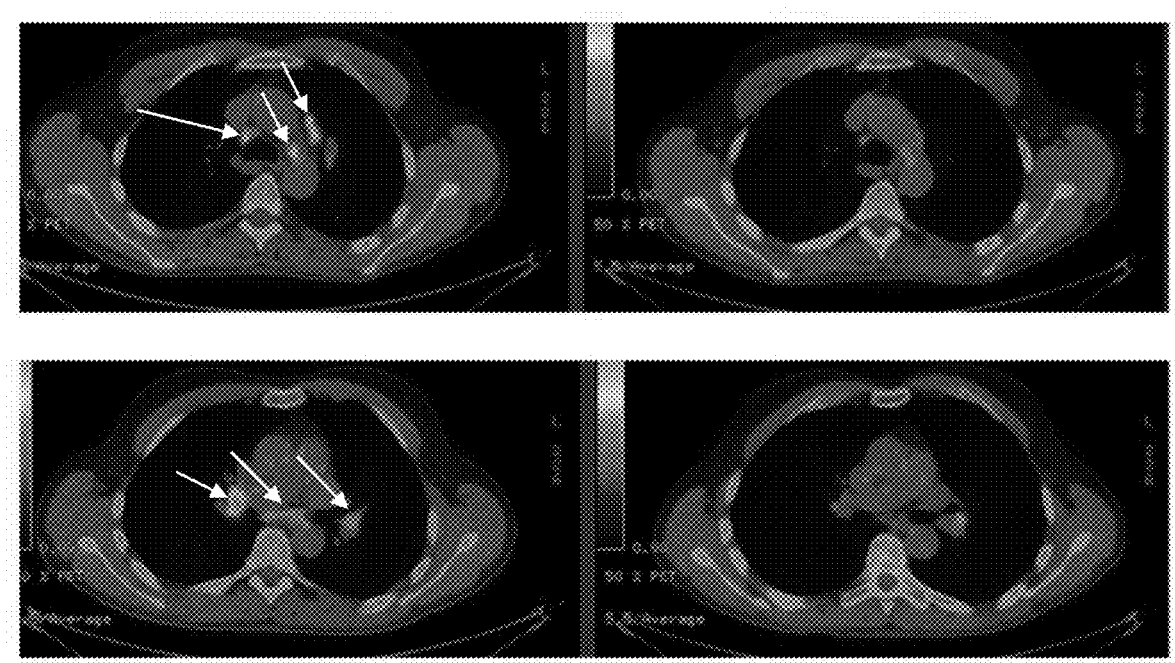
FIG. 6 shows positron emission tomography (PET) scans of a patient who prior to administration of mebendazole was suffering from sarcoidosis. Administration of mebendazole resulted in remission of sarcoidosis.

The mebendazole dose was increased to a daily dose of 400 mg (2×200 mg), and after six weeks a new PET scan was performed, which showed disappearance/reduction in FDG-signal and size (right panel in FIG. 6, compare with same areas in left panel) of the hilar and mediastinal nodes with the radiological diagnosis of sarcoidosis in remission. The serum mebendazole concentration at this time point was 71 ng/ml. In summary, mebendazole was shown to be effective in decreasing the size of the sarcoid tissue in a patient suffering from sarcoidosis.

Example 7. In Vivo Efficacy Study in Systemic Lupus Erythematosus (SLE) in Mice

Materials and Equipment

Dulbecco's phosphate-buffered saline and goat anti-mouse IgG-HRP were obtained from Life Technologies. Methotrexate, calf thymus DNA, poly-L-lysin and TMB solution were obtained from Sigma. Paraformaldehyde 4% and Tween 20 were obtained from Merck. Calf thymus Sm/RNP was obtained from GenWay Biotech. Fetal bovine serum was obtained from Biochrom.

Combur sticks for urine testing were obtained from Swevet. Costar 3590 ELISA plates and V bottom welled dilution plates were obtained from VWR. Microtubes were obtained from VWR and Eppendorf. Microvette 500 Z-Gel and 10 ml tubes were obtained from Sarstedt. 0.6×2.5 mm needles were obtained from Terumo Neolus. 1 ml syringes were obtained from Codan.

Methotrexate was obtained from Sigma-Aldrich (St. Louis, Mo.).

Mebendazole was obtained from Recipharm (Sweden). For oral administration it was dissolved in sesame oil/PBS 1:1 mixture (volume). Sesame oil was obtained from Sigma- Aldrich. As such, the vehicle for the control was sesame oil/PBS 1:1 mixture (volume)

Method and Results

NZBNZWF1 mice spontaneously develop an autoimmune syndrome with notable similarities to human systemic lupus erythematosus (SLE), and thus mice of this type may be used as a model for SLE.

40 female NZBNZWF1 mice (Envigo Europe) were fed and watered ad libitum and acclimatised for approximately 1 week before initiation of the experiment. Mice were 14 weeks old at the initiation of the experiment, and 16 weeks are the start of treatment. The mice were divided into 4 treatment groups of 10 mice each at the initiation of the experiment:

1. Vehicle control: treatment with vehicle only
2. Positive control: treatment with methotrexate (15 mg/kg)
3. Treatment with low dose of mebendazole (25 mg/kg)
4. Treatment with high dose of mebendazole (50 mg/kg)

Treatment groups were mixed between cages to avoid cage effects. Cages held 2 to 10 mice.

The vehicle control treatment and the low and high dose mebendazole treatments were administered orally (p.o) daily for 5 consecutive days per week, for 8 weeks (weeks 16-24 of age of the mice). The positive control treatment of 15 mg/kg methotrexate was administered intraperitoneally 3 times per week for 8 weeks (weeks 16-24 of age of the mice). Table 1 contains full details of the treatment groups.

TABLE 1

Summary of treatment groups

| Treatment group | Treatment | Dose | Administration route | Treatment days | Necropsy week |
|---|---|---|---|---|---|
| Vehicle control | Vehicle | N/A | p.o. | Mon-Fri, 16-24 | Week 30 |
| Positive control | Methotrexate | 15 mg/kg | i.p. | 3 times per week from week 16-24 | Week 30 |
| Low dose mebendazole | Low dose mebendazole | 25 mg/kg | p.o. | Mon-Fri, week 16-24 | Week 30 |
| High dose mebendazole | High dose mebendazole | 50 mg/kg | p.o. | Mon-Fri, week 16-24 | Week 30 |

Mice with wounds that did not heal (determined as "wet wounds" for more than 3 consecutive days) were removed from the experiment. Mice with poor health status (dehydration and kyphotic posture) or showing other severe adverse effects due to drug administration were removed from the experiment.

The weight of the mice was measured weekly during treatment. Spleen weight was determined for all animals at termination of the study. Urine sampling was performed once per month for the first 8 weeks, and then every other week until termination. Serum was collected from all mice at initiation of the experiment (mice age 14 weeks), at start of treatment (mice age 16 weeks), and every second week during treatment (mice age 18, 20, 22, and 24 weeks), after treatment (mice age 26 and 28 weeks) and at termination (mice age 30 weeks). The serum samples were analysed for levels of antibodies directed against double stranded DNA (dsDNA) (anti-ds-DNA antibodies). Anti-(double stranded)-DNA antibodies are highly specific markers of human SLE, and of the autoimmune syndrome in NZBNZWF1 mice. Anti-(double stranded)-DNA antibodies are often found in very high levels in patients with a variety of systemic rheumatic diseases, including SLE, as well as in the autoimmune syndrome in NZBNZWF1 mice.

Figure 7:
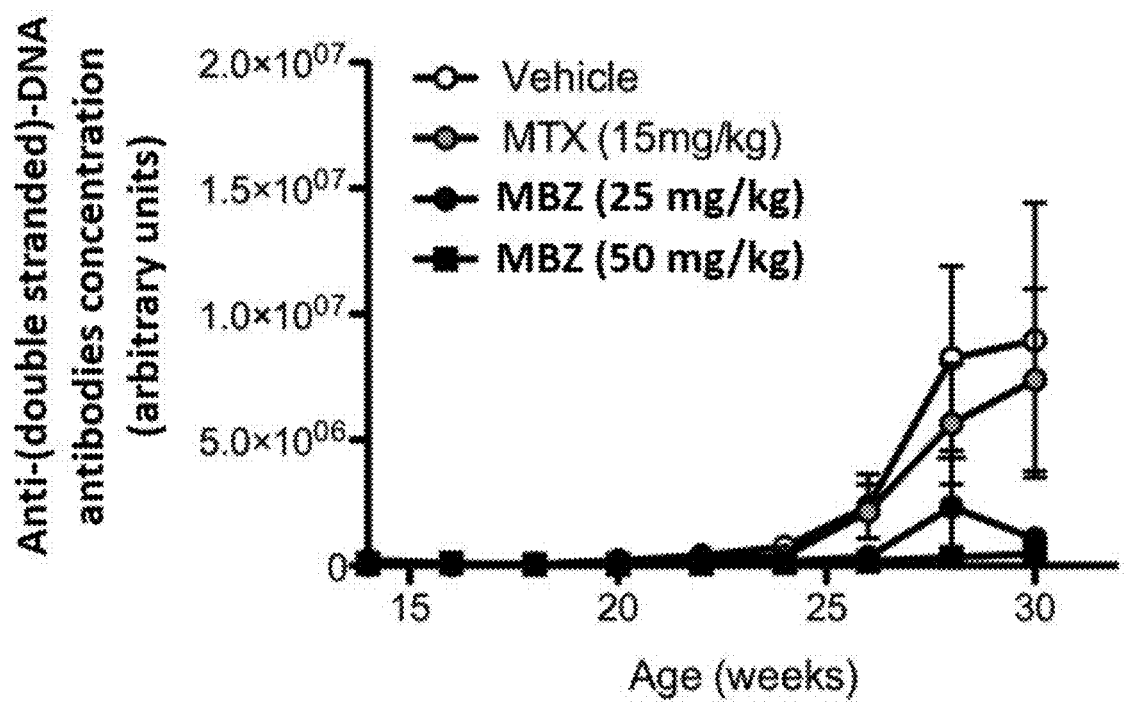
FIG. 7 shows the level of anti-(double stranded)-DNA antibodies in the serum of NZBNZWF1 mice before treatment (week 14), during treatment (week 16 to week 24), and after treatment until termination (week 30) with vehicle, positive control (methotrexate (MTX)) or 25 mg/kg or 50 mg/kg mebendazole (MBZ).

The analysis of serum samples taken during and after the treatment period for anti-ds-DNA antibodies is shown in FIG. 7. As can be seen from FIG. 7, the groups treated with mebendazole (MBZ) showed lower concentrations of anti-dsDNA antibodies in the serum samples than the vehicle control group, or the methotrexate (MTX) positive control group, indicating lower disease activity of SLE in the groups treated with mebendazole. Additionally, the group treated with the higher dose (50 mg/kg) of mebendazole showed a lower concentration of anti-dsDNA antibodies than those treated with the lower dose (25 mg/kg), indicating that the higher dose of mebendazole is more effective in the treatment of SLE.

The invention claimed is:

1. A method for the treatment or prophylaxis of a chronic inflammatory disease, comprising administering an effective amount of mebendazole or a pharmaceutical composition comprising mebendazole to a patient in need thereof, wherein the chronic inflammatory disease is one that is associated with defective ERK signalling.

2. The method of claim 1, wherein said chronic inflammatory disease is an autoimmune disease.

3. The method of claim 1,
wherein said chronic inflammatory disease is associated with increased Type-1 interferon (interferon alpha and/or beta) response from plasmacytoid dendritic cells or other immune cells; and/or
wherein said chronic inflammatory disease is associated with increased p38 MAP kinase signalling.

4. The method of claim 1, wherein said chronic inflammatory disease is any one of systemic lupus erythematosus, sarcoidosis, Huntington's disease, multiple sclerosis, primary biliary cirrhosis, autoimmune hepatitis, Graves' disease, Crohn's disease, ulcerative colitis, coeliac disease, Addison's disease, Sjögren's syndrome and rheumatoid arthritis.

5. The method of claim 1, wherein said chronic inflammatory disease is any one of end stage renal disease, systemic sclerosis (also called scleroderma), myositis, diabetes type 1, psoriasis, tuberculosis, inflammatory bowel disease and Alzheimer's disease.

6. The method of claim 1, wherein the chronic inflammatory disease is characterised by granulomatous inflammation.

7. The method of claim 1, comprising administering to the patient an effective amount of at least one additional active agent selected from the group consisting of non-steroidal anti-inflammatory drugs (NSAIDs), corticosteroids, immunosuppressants and disease-modifying anti-rheumatic drugs (DMARDs).

8. The method of claim 1, wherein the dose of mebendazole administered to the patient is 1 mg to 4000 mg, 10 mg to 3000 mg, 10 mg to 2000 mg, 10 mg to 1000 mg, 10 mg to 750 mg, 10 mg to 500 mg, 20 to 400 mg, 25 mg to 300 mg, or 30 mg to 200 mg.

9. The method of claim 1, wherein the dose of mebendazole administered to the patient achieves a plasma concentration of mebendazole of 1 ng/ml to 1000 ng/ml.

10. The method of claim 1, wherein the dose of mebendazole administered to the patient achieves a plasma concentration of mebendazole of 1 ng/ml to 100 ng/ml.

11. The method of claim 1, wherein the dose of mebendazole administered to the patient achieves a plasma concentration of mebendazole of 60 ng/ml to 80 ng/ml.

12. The method of claim 1, wherein the dose of mebendazole administered to the patient achieves a steady state maximum plasma concentration of 1 ng/ml to 1000 ng/ml.

13. The method of claim 1, wherein said chronic inflammatory disease is systemic lupus erythematosus.

14. The method of claim 1, wherein said chronic inflammatory disease is sarcoidosis.

* * * * *